United States Patent [19]

Larkin et al.

[11] 4,417,082

[45] Nov. 22, 1983

[54] THERMAL TREATMENT OF OLEFIN OLIGOMERS VIA A BORON TRIFLUORIDE PROCESS TO INCREASE THEIR MOLECULAR WEIGHT

[75] Inventors: John M. Larkin; Lewis W. Watts, Jr., both of Austin, Tex.

[73] Assignee: Texaco Inc., White Plains, N.Y.

[21] Appl. No.: 389,740

[22] Filed: Jun. 18, 1982

[51] Int. Cl.$^3$ .............................................. C10L 1/16
[52] U.S. Cl. .................................... 585/10; 585/12; 585/18; 585/255; 585/525
[58] Field of Search .................... 585/10, 12, 18, 255, 585/510, 512, 520, 522, 525, 526, 532, 643, 648, 660, 664

[56] References Cited

U.S. PATENT DOCUMENTS 4,172,855 10/1979 Shubkin et al. ................. 585/255
4,225,739 9/1980 Nipe et al. ....................... 585/525

*Primary Examiner*—Curtis R. Davis
*Attorney, Agent, or Firm*—Jack H. Park; Kenneth R. Priem; David L. Mossman

[57] ABSTRACT

Alpha olefins may be oligomerized over a boron trifluoride catalyst and a protonic promoter, and then held at a temperature between 60° and 150° C. to increase the molecular weight of the oligomers. When the oligomers are hydrogenated they provide a synthetic lubricant base stock having excellent properties. The alpha olefins may be derived from ethylene polymerization or wax pyrolysis. An inert organic solvent may be present.

29 Claims, No Drawings

THERMAL TREATMENT OF OLEFIN OLIGOMERS VIA A BORON TRIFLUORIDE PROCESS TO INCREASE THEIR MOLECULAR WEIGHT

BACKGROUND OF THE INVENTION

1. Field of the Invention

The invention relates to methods of oligomerizing olefins over a boron trifluoride catalyst together with a promoter, and more particularly relates to methods of oligomerizing a mixture of alpha olefins over a boron trifluoride catalyst and then treating them to increase their molecular weight.

2. Description of Related Methods

Nearly all of the patents issued on olefin oligomerization have involved alpha olefins. For example, see U.S. Pat. No. 3,410,925 to Eby, et al. in which alpha olefins are mixed with alkylatable aromatic hydrocarbons over a Friedel-Crafts catalyst to form an alkylation sludge which is then mixed with olefins having 3 to 18 carbon atoms which are also passed over the catalyst to produce olefin dimers. U.S. Pat. No. 3,652,706 to Saines, et al. describes the polymerization of alpha olefins having 2 to 20 carbon atoms over a Friedel-Crafts metal halide catalyst plus a hydrogen form of mordenite to produce compounds having a molecular weight between 700 and 2,500. Production of a gasoline fuel composition is described in U.S. Pat. No. 3,749,560 to Perilstein which occurs by reacting a mixture of mono olefins over a Friedel-Crafts catalyst heated to a temperature around 145° C. to produce oligomers having molecular weights between 350 to 1,500. Also, U.S. Pat. No. 3,149,178 to Hamilton, et al. reveals an improved method for making polymerized olefin synthetic lubricants via a particular distillation technique of oligomers made from alpha mono olefins using a Friedel-Crafts catalyst. Alpha olefins having six to twelve carbon atoms may be dimerized in the presence of a Friedel-Crafts catalyst according to the method described in U.S. Pat. No. 4,172,855 to Shubkin, et al.

It is also known that the term "Friedel-Crafts catalysts" includes boron trifluoride among other metal halide-type Lewis catalysts, see *Kirk-Othmer Encyclopedia of Chemical Technology*, Third Edition, Vol. 11, pg 292. Boron trifluoride has also been known to polymerize olefins, as seen in F. Albert Cotton, et al., *Advanced Inorganic Chemistry: A Comprehensive Text*, Interscience Publishers, 1962, p. 191.

A number of patents have also used $BF_3$ to oligomerize olefins. For example, British Pat. No. 1,323,353 describes the use of wax cracked alpha olefins as precursors for synlube fluids. U.S. Pat. No. 2,780,664 to Serniuk describes the reaction of conjugated dienes with mono olefins over $BF_3$ promoted by an ether mixed with a halo alkane diluent at a temperature from −30° to 100° C. to produce oligomers suitable for drying oils. Alpha olefins having from 5 to 20 carbon atoms are oligomerized using $BF_3$ plus an alcohol or water promoter as described in U.S. Pat. No. 3,382,291 to Brennan. In this patent, $BF_3$ and a mixture of $BF_3$ plus the promoter complex are introduced in two separate streams. Another U.S. patent by Brennan, No. 3,742,082, concerns the dimerization of alpha olefins via $BF_3$ which is promoted with phosphoric acid or water at a temperature from 100° to 150° C. U.S. Pat. No. 3,763,244 to Shubkin, describes the oligomerization of n-alpha olefins having 6 to 16 carbon atoms over $BF_3$ promoted with water, at a temperature between 10° and 60° C. where it is preferred that $BF_3$ is added continuously.

Yet another U.S. patent to Brennan, No. 3,769,363 describes the oligomerization of olefins having 6 to 12 carbon atoms using $BF_3$ with a carboxylic acid promoter having at least 3 carbon atoms at a temperature between 0° and 20° C. to produce olefins heavy in trimer form. U.S. Pat. No. 3,780,128 also to Shubkin relates to the oligomerization of alpha olefins having 6 to 16 carbon atoms in which $BF_3$ is employed in a molar excess of alcohol. U.S. Pat. No. 3,876,720 to Heilman, et al. describes a two-step procedure by which alpha olefins having 8 to 12 carbon atoms are converted to vinylidene olefins which are then reacted over a 1:1 molar complex of $BF_3$ and alcohol to produce oligomerized vinylidene olefins. A method for oligomerizing both short and long chain alpha olefins having from 14 to 20 carbon atoms simultaneously over $BF_3$ with an alcohol or water promoter at 0° to 60° C. with a monomer recycle is described in U.S. Pat. No. 4,225,739 to Nipe, et al. There is also U.S. Pat. No. 4,263,465 to Sheng, et al. which describes a two-step process for reacting 1-butene with a higher alpha olefin over $BF_3$ in the presence of a proton donor at a temperature from −30° to 50° C. to produce an oligomer having 8 to 18 carbon atoms. The intermediate oligomer is reacted with other higher alpha mono olefins over the same catalyst system from −30° to 60° C. to produce oligomers having 20 to 40 carbon atoms. For more information on $BF_3$-catalyzed oligomerization of alpha olefins, see Brennan, "Wide-Temperature Range Synthetic Hydrocarbon Fluids," *Ind. Eng. Chem. Prod. Res. Dev.* 1980, Vol. 19, pp 2–6 and Shubkin, et al., "Olefin Oligomer Synthetic Lubricants: Structure and Mechanism of Formation," *Ind. Eng. Chem. Prod. Res. Dev.* 1980, Vol. 19, pp 15–19.

U.S. Pat. No. 4,213,001 reveals a method of homopolymerizing an alpha olefin by utilizing boron trifluoride under pressure in the presence of a suspended particulate absorbent material. The absorbent material may be silica, alumina, magnesia, zirconia, activated carbon, the zeolites, silicon carbon, silicon nitride, titania, thoria, porous polyvinyl alcohol beads, porous polyethylene glycol beads and the like.

Additional methods in this field include that of U.S. Pat. No. 4,045,507 which involves a multi-stage, continuous process for polymerizing alpha olefins in the presence of boron trifluoride and a co-catalyst. A process involving the copolymerization of propylene or propylene plus higher alpha olefins with small amounts of ethylene in the presence of a vanadium-containing catalyst, an aluminum-containing catalyst, and a Friedel-Crafts catalyst is described in U.S. Pat. No. 4,182,922 and may be of particular interest. U.S. Pat. No. 4,263,465 involves the preparation of a low viscosity synthetic lubricant by polymerizing 1-butene to an oligomer containing a number average of about 8 to 18 carbon atoms and copolymerizing the oligomer with an alphamono olefin having 8 to 18 carbon atoms to produce a copolymer having an average of about 20 to 40 carbon atoms.

U.S. Pat. No. 4,300,006 issued on Nov. 10, 1981. It describes a process for producing a hydrocarbon oil by contacting a mixture of alpha and at least 50 weight percent internal olefins with a boron trifluoride dimerization catalyst. However, the productivity of useful products from the process revealed in U.S. Pat. No.

4,300,006 is quite low. For example, an alkane diluent is found to be necessary in the process described therein. When the lights and heavies are distilled out as required by the method, little useful product results. Further, this method requires a much longer reaction time and a higher catalyst concentration than desired. It would be beneficial if a method for producing synthetic lubricants could be devised which would overcome the aforementioned disadvantages.

Also of interest in U.S. Pat. No. 4,214,112. It discloses a process for producing an olefin oligomer which involves polymerizing olefins having not less than 6 carbon atoms in the presence of a specified catalyst system. The system consists of an aluminum halide, a polyhydric alcohol derivative and a nickel compound or a cobalt compound. The nickel and cobalt compounds are listed as nickel carbonate, nickel tetracarbonyl, nickel nitrate, nickel monoxide, trinickel tetroxide, nickel sequioxide, nickel hydroxide, nickel sulfide, nickel sulfate, nickel acetate, nickel oleate, nickel stearate, nickel diatomaceous earth, nickel chloride, nickel acetylacetonate, nickel peroxide, cobalt carbonate, dicobalt octacarbonyl, cobalt chloride, cobalt nitrate, cobalt oxide, cobalt hydroxide, cobalt sulfide, cobalt sulfate, cobalt acetate, cobalt oleate, cobalt acetylacetonate, etc. and combinations thereof. The compounds used in the examples therein are nickel oxide, nickel chloride, nickel oleate, nickel carbonate and cobalt chloride.

In the field of oligomerizing olefins for synthetic lubricants, it is a continual problem to produce olefins having low viscosities at room temperature and below but which have a high viscosity index and low volatility.

SUMMARY OF THE INVENTION

The invention is concerned with a process for oligomerizing mono olefins comprising contacting a mixture of alpha mono olefins which consists essentially of greater than 50 weight percent of at least one low molecular weight alpha olefin having 4 to 6 carbon atoms and less than 50 weight percent of at least one higher molecular weight alpha olefin having 8 to 18 carbon atoms, with a catalyst comprising boron trifluoride at a temperature between about 25° and 60° C. The resulting mixture is subsequently held for a period of time at a temperature between about 60° and 150° C.

DESCRIPTION OF THE PREFERRED EMBODIMENTS

It has been surprisingly discovered that oligomers which have an unusual blend of properties may be made by reacting predominantly low molecular weight alpha mono olefins over a boron trifluoride catalyst and a protonic promoter and then holding them at an elevated temperature. No other researchers have accomplished this objective in this way.

The olefin feedstock may be generally expressed as a mixture of alpha olefins having the formula

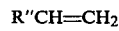
R"CH=CH$_2$ where R" is an alkyl radical of 2 to 4 carbon atoms for the low molecular weight olefins and 6 to 16 carbon atoms for the higher molecular weight alpha olefins. It is especially preferred that the two sizes of olefins be used together; namely, at least one alpha olefin having 4 to 6 carbon atoms (1-butene, 1-pentene, and 1-hexene) and at least one higher molecular weight alpha olefin having 8 to 18 carbon atoms. This combination of low and high molecular weight olefins helps contribute to the unique properties of the resulting oligomers. It is also preferred that the majority of the olefin reactant mixture be the low molecular weight alpha olefins. It is especially preferred that the low molecular weight alpha olefin be 1-butene and the higher molecular weight olefins have 10 to 18 carbon atoms.

The higher alpha olefins to be oligomerized in this invention may be obtained by a multi-step process. In the first step, ethylene is transformed into linear alpha olefins using Ziegler technology as disclosed in various patents, including U.S. Pat. Nos. 3,424,815; 3,482,000; 3,424,816; 3,444,264; 3,444,263; 3,502,741; 3,510,539; 3,478,124; and 3,441,631. These patents are incorporated herein by reference. The result of this conversion of ethylene is a mixture of alpha olefins ranging from C-4 to above C-24. The alpha olefins ranging from about C-4 or C-8 to C-18 or any other range of alpha olefins desired within C-4 to C-24 are separated and oligomerized using boron trifluoride and the promoter of this invention. The alpha olefins of below about 8 and above about 18 carbon atoms are combined and subjected to an isomerization/disproportionation process described in the literature, for example: U.S. Pat. Nos. 3,647,906; 3,728,414 and 3,726,938, which are incorporated herein by reference.

The olefins resulting from this isomerization/disproportionation process are a mixture of alpha and internal olefins of various molecular weights. The olefins having a total number of carbon atoms in the range from about 8 to 18 or any selected cut within that range may be oligomerized with boron trifluoride and a protonic promoter. Those olefins may be mixed with the alpha olefins from the initial ethylene made feed and oligomerized.

Such a process provides a systematic way to control which olefin cut is selected for oligomerization, and also uses the discarded cuts for additional feed. Olefins useful in the method of this invention may also be produced by wax pyrolysis.

Generally, the weight ratio of the low molecular weight alpha olefins (C$_4$–C$_6$) to the higher molecular weight alpha olefins is preferred to range from greater than 1:1 to 3:1.

The catalyst of choice is boron trifluoride. However, it is well known that boron trifluoride by itself is not very effective and promoters (sometimes called cocatalysts) must be employed to activate the boron trifluoride. The most effective promoters for the method of this invention are alcohols, carboxylic acids and water. A preferred promoter for this invention is 1-butanol. The promoter must be protonic to be effective.

It is preferred that the boron trifluoride catalyst be present in an amount of from 0.75 to 3.0 weight percent, based on the olefin mixture amount. One skilled in the art may find an inert, organic solvent, such as cyclohexane, useful in conducting the oligomerization. However, the amount of solvent should be less than about 50 weight percent based on the olefin mixture. The temperature range at which the oligomerization may be performed successfully is between 27° and 75° C., with a preferred range between 30° to 60° C.

It was surprisingly discovered that the molecular weight of the olefin oligomers may be increased by holding the oligomers for a period of time at an elevated temperature. Preferably, the elevated temperature is about 60° to 150° C., where an especially preferred range is from about 90° to 150° C. The holding period should be long relative to the oligomerization period with an acceptable length of time being about two hours or more. It will be demonstrated that the use of a two-stage process, starting with a low temperature for oligomerization and a high temperature for a finishing, holding period, gives better results (higher molecular weight products) than if both stages were at the same temperature, either high or low.

The pressure range of the reaction may run from zero to 1,000 psig although autogenous pressures are preferred. The pressure should be sufficient to maintain a liquid phase reaction. The oligomerization of the olefins may be conducted in a batch or continuous mode.

In order to form materials which have adequate oxidative stability for lubricants, the oligomerized olefins are optionally hydrogenated either partially or totally. This hydrogenation is done by procedures known to those skilled in the art as exemplified by U.S. Pat. Nos. 4,045,508; 4,013,736; 3,997,622 and 3,997,621. A particularly preferred catalyst for this hydrogenation is a nickel-copper-chromium oxide catalyst described in U.S. Pat. No. 3,152,998, incorporated herein by reference. A cobalt-copper-chromium oxide catalyst would also be useful.

Kinematic viscosities at the standard temperature of 210° F. are given in centistokes. The synthetic lubricant components of this invention have kinematic viscosities between 3.5 and 7.0 centistokes. The viscosity index (VI) is the change in viscosity with temperature such that the higher the number, the lower is the change in viscosity with temperature. Conversely, a low VI signifies a large change in viscosity with temperature. Pour point is a measure of the temperature, in degrees Centigrade, at which the sample will begin to pour. Below that temperature the composition may generally be regarded as a solid. Thermogravimetric analysis (TGA) is a test which measures volatility by measuring the weight percent of sample remaining at various temperatures as the temperature is raised in a slow, uniform manner. When a sample's TGA indicates that at least 80% remains at 233° C., the sample is considered sufficiently non-volatile to be useful in lube oil formulations.

Synthetic lubricant components which are expected to be used as lubricants should contain olefin oligomers having about twenty carbon atoms and greater. Thus, the only preferred separation step is to remove all olefin oligomers having less than about twenty carbon atoms. These lower carbon number oligomers may be removed before or after the hydrogenation step.

The process of this invention is further illustrated by the following examples.

EXAMPLE 1

Addition of 4/1/1 Weight Ratio C-4/C-10/C-14 Alpha Olefins To Cyclohexane/BF$_3$/1-Butanol at 34° C. Followed by 120° C. for Two Hours.

To a mixture of 415 g cyclohexane and 21 g BF$_3$ contained in a 1-gallon stirred autoclave, there was added 1250 g of the 4/1/1, C-4/C-10/C-14 alpha olefins (which also contained 13.63 g of 1-butanol) over a two-hour period at an average temperature of 34° C. After one-half hour of stirring at 30°–34° C., the temperature was raised to 120° C. and maintained at 120°–121° C. for two hours. The mixture was cooled to 37° C., quenched with water, and washed repeatedly with water. Removal of the cyclohexane (rotary evaporator, 97° C., 38 mm Hg) left an oligomer with an average carbon number (wt. average) of 37.1913; 4% of the molecules were less than or equal to C-20.

Kinematic viscosity @25° C., 100° F., and 210° F. was 36.81, 21.55, 4.15 cS, respectively.

Viscosity index = 104.9

Pour Point < −50° F.

Hydrogenation and removal of 13% of the hydrogenated product overhead provided a liquid with kinematic viscosity at 25° C., 100° F., and 210° F. of 64.1, 34.8, and 5.44 cS, respectively, and a pour point of −35° F.; where the VI was 99.8. In thermogravimetric analysis (+10° C./min. in flowing nitrogen), 89% of the sample remained at 233° C.

EXAMPLE 2

Omission of Thermal Treatment

The procedure of Example 1 was essentially repeated, except that the 120° C. treatment was omitted. The average carbon number of the oligomer was 28.6 with 25% of the molecules less than or equal to C-20. In Example 1, the average carbon number was about 37.2 and only 4% of the molecules had less than or equal to 20 carbon atoms. The much improved values of the material from Example 1 show the necessity of the subsequent heat treatment step.

EXAMPLE 3

Comparative Example: Addition of 4/1/1 Weight Ratio C-4/C-10/C-14 Alpha-Olefins to Cyclohexane/BF$_3$/1-Butanol At 116° C. Followed By 120° C. for Two Hours.

The procedure of Example 1 was essentially repeated, except that the olefin/1-butanol mixture was introduced at 112°–120° C. (average=116° C.) instead of at 34° C. The average carbon number was 20.3 with 75% of the molecules less than or equal to C-20. Thus, this example illustrates necessity for forming the oligomer at a lower temperature prior to heating.

EXAMPLE 4

Addition of 4/1/1 Weight Ratio C-4/C-10/C-14 Alpha-Olefins to Cyclohexane/BF$_3$/1-Butanol at 31° C. Followed By Two Hours at 97° C.

The procedure of Example 1 was essentially repeated with olefin introduction at 31° C. and two hours thermal treatment at 97° C. The average carbon number was 30.9 with approximately 8% of the molecules less than or equal to C-20. This example illustrates that heating at a lower temperature results in a lower molecular weight oligomer, thus allowing "tailoring" of the properties by adjustment of the temperature of thermal treatment.

Hydrogenation and removal of 6% of the hydrogenated oligomer overhead provided a liquid with a kinematic viscosity at 25° C., 100° F., and 210° F. of 52.36, 29.63, and 4.91 cS, respectively. The pour point was −50° F., and the viscosity index was 96.2. In thermogravimetric analysis as in Example 1, 80% of the sample remained at 233° C.

EXAMPLE 5

The procedure of Example 1 was essentially repeated with the following modifications: Only 14 g BF$_3$ and only 6.85 g 1-butanol were used; also 12.0 g of nickel-copper-chromium oxide catalyst (described in U.S. Pat. No. 3,152,998) in reduced form were present in the autoclave. After two hours at 120° C., a sample was withdrawn, quenched with excess water, and worked up as in Example 1. The product had an average carbon number of 28.6 with 15% less than or equal to C-20. The remainder of the product was kept at 120° C. for two additional hours. Its average carbon number was 30.3 with 14% less than or equal to C-20.

This example illustrates that the increase in molecular weight as a result of thermal treatment is a function of time.

These and other examples are summarized in Table I.

TABLE I

THERMAL TREATMENT DURING OLIGOMERIZATION

| Wt. % BF$_3$ | Addition Temp. °C. | Holding Temp. °C. | Holding Time (hrs.) | Wt. Avg. Carbon No. | Approx. % below C$_{20}$ |
|---|---|---|---|---|---|
| 1.68 | 34 | 120 | 2 | 37 | 4 |
| 1.68 | 34 | — | — | 28.6 | 25 |
| 1.60 | 116 | 120 | 2 | 20.3 | 75 |
| 1.60 | 31 | 97 | 2 | 31 | 8 |
| 1.12[a] | 34 | 120 | 2 | 28.6 | 15 |
|  |  |  | 2 | 30.3 | 14 |
| 1.84 | 34 | 34 | 2 | 21 | 70 |
| 1.60 | 34 | 34 | 1.1[b] | 19 | 84 |
| 1.68[c] | 33 | 120 | 2 | 25 | 30 |
| 0.8 | 32 | 32 | 2 | 17 | 92 |
| 0.8 | 32 | 120 | 2 | 19 | 85 |

[a] 12.0 g of Ni—Cu—Cr catalyst also present.
[b] Only one hour addition time.
[c] NAFION® perfluorosulfonic acid resin catalyst was also present; no beneficial effect observed.

Inspection of the liquid chromatographic data indicates the increase in molecular weight is derived mainly from conversion of the lower oligomers to those in the mid-range. Very little heavier oligomers are produced indicating the already heavy molecules are less susceptible to further oligomerization at high temperature than the light molecules. This is a fortunate circumstance, since it results in the increased yield of narrow molecular weight range oligomers.

Many modifications may be made in the method of this invention without departing from its scope which is defined only by the appended claims. For example, it would be expected that one skilled in the art could change the BF$_3$ promoter, the temperature, the pressure or the modes of addition from those actually employed herein in trying to maximize the conversion or optimize the oligomer properties.

We claim:

1. A process for oligomerizing mono olefins comprising
 a. contacting a mixture of alpha mono olefins which consists essentially of
   (1) greater than 50 weight percent of at least one low molecular weight alpha olefin having 4 to 6 carbon atoms and
   (2) less than 50 weight percent of at least one higher molecular weight alpha olefin having 8 to 18 carbon atoms,
   with a catalyst comprising boron trifluoride at a temperature between about 25° C. and 60° C., and
 b. subsequently holding the resulting mixture for at least two hours at a temperature between about 60° and 150° C.

2. The process of claim 1 in which the weight ratio of the low molecular weight alpha olefin to the higher molecular weight alpha olefin ranges from greater than 1:1 to 3:1.

3. The process of claim 1 in which the low molecular weight olefin is 1-butene and the higher molecular weight olefin has 10 to 18 carbon atoms.

4. The process of claim 1 in which an organic, protonic promoter is present in conjunction with the boron trifluoride catalyst, said promoter being selected from the group consisting of alcohols and carboxylic acids.

5. The process of claim 4 in which the protonic promoter is 1-butanol.

6. The process of claim 1 in which the catalyst is present in an amount of from 0.75 to 3.0 weight percent, based on the olefin mixture.

7. The process of claim 1 in which less than 50 weight percent of an inert, organic solvent is employed, based on the olefin mixture.

8. The process of claim 1 in which the holding step is conducted at a temperature between about 90° and 150° C.

9. The process of claim 1 in which the oligomerized olefins are subsequently hydrogenated.

10. A process for oligomerizing mono olefins comprising
 a. contacting a mixture of alpha mono olefins which consists essentially of
   (1) greater than 50 weight percent of at least one low molecular weight alpha olefin having 4 to 6 carbon atoms and
   (2) less than 50 weight percent of at least one higher molecular weight alpha olefin having 8 to 18 carbon atoms, with a catalyst comprising boron trifluoride together with a protonic promoter, in which the catalyst is present in an amount of from 0.75 to 3.0 weight percent, based on the olefin mixture, at a temperature between about 25° and 60° C., and
 b. subsequently holding the resulting mixture for at least two hours between about 60° and 150° C.

11. The process of claim 10 in which the weight ratio of the low molecular weight alpha olefin to the higher molecular weight alpha olefin ranges from greater than 1:1 to 3:1.

12. The process of claim 10 in which the low molecular weight olefin is 1-butene and the higher molecular weight olefin has 10 to 18 carbon atoms.

13. The process of claim 10 in which the organic, protonic promoter is selected from the group consisting of alcohols and carboxylic acids.

14. The process of claim 13 in which the organic, protonic promoter is 1-butanol.

15. The process of claim 10 in which less than 50 weight percent of an inert, organic solvent is employed, based on the olefin mixture.

16. The process of claim 10 in which the holding step is conducted at a temperature between about 90° and 150° C.

17. The process of claim 10 in which the oligomerized olefins are subsequently hydrogenated.

18. A process for oligomerizing mono olefins comprising
 a. contacting a mixture of alpha mono olefins which consists essentially of
   (1) at least one low molecular weight alpha olefin having 4 to 6 carbon atoms and
   (2) at least one higher molecular weight alpha olefin having 8 to 18 carbon atoms, the weight ratio of the low molecular weight alpha olefin to the higher molecular weight alpha olefin being from greater than 1:1 to 3:1, with a catalyst comprising boron trifluoride together with a protonic promoter selected from the group consisting of alcohols and carboxylic acids, in which the catalyst is present in an amount of from 0.75 to 3.0 weight percent based on the olefin mixture, at a temperature between about 25° and 60° C., and b. subsequently holding the resulting mixture at a temperature between about 90° and 150° C. for at least two hours.

19. A process for oligomerizing mono olefins comprising a. contacting a mixture of alpha mono olefins which consists essentially of
  (1) 1-butene and
  (2) at least one higher molecular weight alpha olefin having 10 to 18 carbon atoms, the weight ratio of 1-butene to the higher molecular weight alpha olefin being from greater than 1:1 to 3:1,
with a catalyst comprising boron trifluoride together with 1-butanol as a protonic promoter, in which the catalyst is present in an amount of from 0.75 to 3.0 weight percent based on the olefin mixture, at a temperature between about 25° and 60° C., and b. subsequently holding the resulting mixture at a temperature between about 90° and 150° C. for at least two hours.

20. The process of claim 18 or 19 in which less than 50 weight percent of an inert, organic solvent is employed, based on the olefin mixture.

21. The process of claim 18 or 19 in which the oligomerized olefins are subsequently hydrogenated.

22. A process for the production of a synthetic lubricant component comprising a. contacting a mixture of alpha mono olefins which consists essentially of
  (1) at least one low molecular weight alpha olefin having 4 to 6 carbon atoms and
  (2) at least one higher molecular weight alpha olefin having 8 to 18 carbon atoms, the weight ratio of the low molecular weight alpha olefin being from greater than 1:1 to 3:1,
with a catalyst comprising boron trifluoride together with a protonic promoter selected from the group consisting of alcohols and carboxylic acids, in which the catalyst is present in an amount of from 0.75 to 3.0 weight percent based on the olefin mixture at a temperature between about 25° and 60° C., b. subsequently holding the resulting mixture at a temperature between about 90° and 150° C. for at least two hours, c. neutralizing the resulting crude oligomer product, d. removing the organic layer from the neutralized crude oligomer product, e. hydrogenating the oligomers in the removed organic layer, and f. stripping off the molecules having less than 20 carbon atoms, the balance being the synthetic lubricant component.

23. The process of claim 22 in which the low molecular weight olefin is 1-butene and the higher molecular weight olefin has 10 to 18 carbon atoms.

24. The process of claim 22 in which the protonic promoter is 1-butanol.

25. The process of claim 22 in which less 50 weight percent of an inert, organic solvent is employed, based on the olefin mixture.

26. A synthetic lubricant component having a kinematic viscosity at 210° F. of between 3.5 and 7.0 centistokes being produced by oligomerizing a mixture of mono olefins by a process comprising a. contacting a mixture of alpha mono olefins which consists essentially of
  (1) 1-butene and
  (2) at least one higher molecular weight alpha olefin having 10 to 18 carbon atoms, the weight ratio of 1-butene to the higher molecular weight alpha olefin being from greater than 1:1 to 3:1,
with a catalyst comprising boron trifluoride together with a protonic promoter, in which the catalyst is present in an amount of from 0.75 to 3.0 weight percent based on the olefin mixture, at a temperature between about 25° and 60° C., b. subsequently holding the resulting mixture at a temperature between about 90° and 150° C. for at least two hours, and c. subsequently hydrogenating the oligomerized olefins.

27. The synthetic lubricating component of claim 28 in which in the process for making the component, the protonic promoter is selected from the group consisting of alcohols and carboxylic acids.

28. The synthetic lubricating component of claim 27 in which the protonic promoter is 1-butanol.

29. The synthetic lubricating component of claim 26 in which in the process for making the component, less than 50 weight percent of an inert, organic solvent is employed, based on the olefin mixture.

* * * * *